(12) United States Patent
Bennett et al.

(10) Patent No.: US 11,992,345 B2
(45) Date of Patent: May 28, 2024

(54) METHOD AND SYSTEM FOR ADJUSTING AUDIO SIGNALS BASED ON MOTION DEVIATION

(71) Applicant: University of Miami, Miami, FL (US)

(72) Inventors: Christopher Bennett, Miami, FL (US); Robert Gailey, Miami, FL (US); Vibhor Agrawal, Miami, FL (US); Colby Leider, Homestead, FL (US)

(73) Assignee: University of Miami, Miami, FL (US)

( * ) Notice: Subject to any disclaimer, the term of this patent is extended or adjusted under 35 U.S.C. 154(b) by 373 days.

(21) Appl. No.: 15/932,190

(22) PCT Filed: Aug. 17, 2016

(86) PCT No.: PCT/US2016/047426
§ 371 (c)(1),
(2) Date: Feb. 16, 2018

(87) PCT Pub. No.: WO2017/031247
PCT Pub. Date: Feb. 23, 2017

(65) Prior Publication Data
US 2019/0099134 A1 Apr. 4, 2019

Related U.S. Application Data

(60) Provisional application No. 62/206,575, filed on Aug. 18, 2015.

(51) Int. Cl.
*A61B 5/00* (2006.01)
*A61B 5/11* (2006.01)
(Continued)

(52) U.S. Cl.
CPC .............. *A61B 5/7415* (2013.01); *A61B 5/11* (2013.01); *A61B 5/1118* (2013.01); *A61B 5/112* (2013.01);
(Continued)

(58) Field of Classification Search
CPC ....... A61B 5/7415; A61B 5/11; A61B 5/1116; A61B 5/1118; A61B 5/112; A61B 5/1121; A61B 5/1123
(Continued)

(56) References Cited

U.S. PATENT DOCUMENTS

| 5,679,004 A | 10/1997 | McGowan et al. |
| 5,730,140 A * | 3/1998 | Fitch .................... A61B 5/0205 600/514 |

(Continued)

FOREIGN PATENT DOCUMENTS

WO    WO 2005/086574    9/2005

OTHER PUBLICATIONS

European Search Report and Written Opinion dated Feb. 18, 2019 regarding European Application No. 16837783.6, 7 pages.
(Continued)

*Primary Examiner* — Christian Jang
(74) *Attorney, Agent, or Firm* — Knobbe, Martens, Olson & Bear, LLP

(57) ABSTRACT

A system measures performance activity of a user using a motion capture device, such as one or more knee sleeves each a plurality of inertial-measurement unit. Captured motion characteristic data is classified against previously captured data and then mapped to particular audio effects, which are then altered in different ways depending on the classification and provided the user. The audio feedback works to improve the user's performance of the activity by changing between negative and positive feedback depending on the user's performance. The system regularly measures the motion capture data, altering audio effects provided to the user, until the user reaches an improvement goal.

32 Claims, 8 Drawing Sheets

(51) Int. Cl.
*G06N 3/02* (2006.01)
*G06N 20/00* (2019.01)
*G10H 1/00* (2006.01)
*G10L 21/003* (2013.01)
*G16H 20/30* (2018.01)
*G16H 40/67* (2018.01)
*G16H 50/20* (2018.01)
*H04N 19/10* (2014.01)

(52) U.S. Cl.
CPC .......... *A61B 5/1124* (2013.01); *A61B 5/486* (2013.01); *G06N 3/02* (2013.01); *G06N 20/00* (2019.01); *G10H 1/0091* (2013.01); *G16H 20/30* (2018.01); *G16H 40/67* (2018.01); *G16H 50/20* (2018.01); *H04N 19/10* (2014.11); *A61B 5/6828* (2013.01); *A61B 2505/09* (2013.01); *G10H 2210/221* (2013.01); *G10H 2210/311* (2013.01); *G10H 2220/201* (2013.01); *G10H 2220/321* (2013.01); *G10H 2220/391* (2013.01); *G10H 2220/395* (2013.01); *G10L 21/003* (2013.01)

(58) Field of Classification Search
USPC ....................................................... 600/587
See application file for complete search history.

(56) References Cited

U.S. PATENT DOCUMENTS

| | | | | |
|---|---|---|---|---|
| 5,919,149 | A * | 7/1999 | Allum | A61B 5/1116 600/595 |
| 7,794,505 | B2 | 9/2010 | Clausen et al. | |
| 2004/0116837 | A1 * | 6/2004 | Yamaguchi | A63B 69/0028 600/595 |
| 2011/0166488 | A1 * | 7/2011 | Miyake | A61H 3/00 601/34 |
| 2011/0184225 | A1 * | 7/2011 | Whitall | A63B 24/0003 600/28 |
| 2011/0184255 | A1 | 7/2011 | Whitall et al. | |
| 2013/0131555 | A1 | 5/2013 | Hook et al. | |
| 2014/0180632 | A1 * | 6/2014 | Yataka | A61B 5/1126 702/153 |
| 2015/0066104 | A1 | 3/2015 | Wingeier et al. | |
| 2015/0081066 | A1 * | 3/2015 | Yeh | H04L 63/0853 700/94 |
| 2015/0133821 | A1 * | 5/2015 | Pusch | A61B 5/1122 600/595 |
| 2015/0313496 | A1 * | 11/2015 | Connor | A61B 5/0476 600/301 |
| 2016/0067584 | A1 * | 3/2016 | Giedwoyn | G16H 40/67 700/91 |
| 2016/0133152 | A1 * | 5/2016 | Arif | G09B 5/00 434/247 |
| 2016/0180440 | A1 * | 6/2016 | Dibenedetto | G06Q 30/02 705/26.7 |

OTHER PUBLICATIONS

PCT Search Report and Written Opinion dated Oct. 28, 2016 regarding International Application No. PCT/US2016/047426, 9 pages.

* cited by examiner

METHOD AND SYSTEM FOR ADJUSTING AUDIO SIGNALS BASED ON MOTION DEVIATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present disclosure relates to adjusting audio signals and, more particularly, using adjustable audio signals in a feedback manner to improve a subject's kinematic, kinetic, spatial and/or temporal motion performance.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

During rehabilitation, exercise, training, recreational activity, or therapy proper execution of a prescribed routine is paramount to successful completion. For example, during rehabilitation of gait (from stroke, partial paralysis, amputation, etc.) maintenance of proper symmetry between the two legs is an important basic concept. During exercise and training, reaching target range of motion of the limbs is required in order to progress to the next stage or achieve a goal. Collectively, these examples are part of repeated and targeted human kinematic, kinetic, spatial and/or temporal kinematic motions.

The use of an audio signal to guide kinematic motions has been shown to improve focus during a variety of tasks. This phenomenon is enhanced when the audio signal is representative of the kinematic motions being performed. In this case, it is known as audio bio-feedback. Audio bio-feedback systems have been previously used to condition balance and motor coordination in response to kinematic motions of a user. In these previous studies, kinematic motions have been represented by synthesized tones or sounds, a process known as sonification. For example, if the range of motion of a joint was being monitored by a kinematic acquisition device, then an ascending scale of tones might be sonified at every ten degree interval achieved by the user.

While sonification is an effective form of audio bio-feedback, it cannot be easily embedded in an audio source without severely affecting audibility. For example, if the user is listening to music, then the presence of an additional sonification audio source (as described above) would result in the complete disruption of both audio sources. However, audio signals can be embedded within a music signal in the form of audio effects (Fx). Audio Fx are changes or modulations to the audio source that result in perceivable differences. For example, amplitude modulation (AM) is an audio Fx with two adjustable parameters: AM depth and AM frequency. Manipulation of these parameters results in a vibrato effect to an underlying audio source, such as music. Furthermore, audio Fx have varying degrees or intensity of application. In the case of AM, the depth is controllable from 0% to 100%, and the AM frequency is controllable from 0 Hz up to 16 Hz.

The principles of audio bio-feedback can be utilized with audio Fx applied to a music source. In sonification, a progression of tones (such as a scale) is used to map to a progression of kinematic motion. In the case of audio Fx, kinematic motions are mapped to a particular audio Fx in order to provide audio bio-feedback to the user. Audio Fx may inherently degrade the underlying audio source (as in AM), or the audio Fx may perceptually improve the underlying audio source (as in a low-frequency enhancer, or "bass boost"). This provides the user a reward or penalty to the audio source, such as music, based on the performance of kinematic motion.

SUMMARY OF THE INVENTION

In accordance with an example, a system to control an audio signal that is to be provided to a subject in response to changes in motion patterns of the subject, the system comprising: one or more processors; one or more memories; a sensor module stored on the one or more memories and adapted to receive sensor motion data of the subject from one or more kinematic, kinetic, spatial and/or temporal sensors coupled to the system; a motion analysis module stored on the one or more memories and adapted to cause the one or more processors to analyze the sensor motion data and determine an amount of deviation of the sensor motion data from baseline motion data for each of one or more motion characteristics, wherein the determining produces a set of deviated sensor motion characteristics with values; a perceptual mapping module stored on the one or more memories and adapted to cause the one or more processors to map the set of deviated sensor motion characteristics to one or more characteristics of the audio signal to be provided to the subject, wherein the mapping produces a set of mapped characteristics of the audio signal; and an audio effects module stored on the one or more memories and adapted to cause the one or more processors to adjust values of each of the set of mapped characteristics based on the deviation values of the set of deviated sensor motion characteristics, wherein the adjusting produces an audio signal effects model to be applied to the audio signal.

In accordance with another example, a computer-implemented method to control an audio signal that is to be provided to a subject in response to changes in motion patterns of the subject, the method comprising: receiving, at a sensor module stored on one or more memories, sensor motion data of the subject from one or more kinematic, kinetic, spatial and/or temporal sensors coupled to the sensor module; analyzing, in a motion analysis module stored on the one or more memories, the sensor motion data and determining an amount of deviation of the sensor motion data from baseline motion data for each of one or more motion characteristics, wherein the determining produces a set of deviated sensor motion characteristics with values; mapping, in a perceptual mapping module stored on the one or more memories, the set of deviated sensor motion characteristics to one or more characteristics of the audio signal to be provided to the subject, wherein the mapping produces a set of mapped characteristics of the audio signal; and adjusting, in an audio effects module stored on the one or more memories, values of each of the set of mapped characteristics based on the deviation values of the set of deviated sensor motion characteristics to produce an altered version of the audio signal.

In some examples, the system includes an audio signal source; the method includes use of an audio signal source.

The audio signal source may be adapted to produce audio signals and may be coupled to the audio effects module, which causes the audio signal source to alter the audio signal using the audio signal effects model to produce an altered version of the audio signal.

In some examples, the audio effects module is adapted to perform an amplitude modulation, frequency modulation, distortion, bitcrushing, chorus, ducking, frequency filtering, spatialization, localization, panning, reverb, echo, compression, expanding, phasing, pitch-shifting, flanging, gating, vocoding, and/or delay on the audio signal.

In some examples, the audio effects module is adapted to perform a high-pass filtering, a band-pass filtering, a low-shelf filtering, a high-shelf filtering, or a band-stop filtering.

In some examples, a sensor module is adapted to collect sensor motion data of the subject as the subject is provided the altered version of the audio signal.

In some examples, the sensor module is adapted to supply updated sensor motion data of the subject to a motion analysis module. In some examples, an updated amount of deviation of the updated sensor motion data from a baseline motion data is determined by the system. In some examples, the updated amount of deviation is determined for one or more motion characteristics.

In some examples, the audio signal contains music.

In some examples, the audio effects module adjusts the values of each of a set of mapped characteristics using a neural network, Bayesian or other probabilistic classifier, support vector machine, linear/quadratic discriminant analysis machine, clustering algorithm, deep learning method, and/or an ensemble method.

In some examples, the motion characteristics comprise gait speed, step width, step length, stance time, gait phase, symmetry of the limbs, inertial motions of the limbs, cadence, path of pressure, path of center of mass, ground reaction force, lower limb or sacral trajectory, and/or trunk orientation.

In some examples, the motion characteristics comprise trunk flexion/extension, hip Flexion/extension, knee flexion/extension, foot-floor angle at heel contact, ankle plantarflexion/dorsiflexion, and/or energy expenditure.

In some examples, the perceptual mapping module is adapted to map each of the deviated sensor motion characteristics to one the mapped characteristics of the audio signal.

In some examples, the perceptual mapping module is adapted to map at least one of the deviated sensor motion characteristics to more than one of the mapped characteristics of the audio signal.

In some examples, the system and method are used for improving, for a user, one or more motion characteristics associated with rehabilitation.

In some examples, the system and method are used for improving, for a user, one or more motion characteristics associated with sports performance.

In some examples, a user's motion characteristic performance is measured against a previously measured baseline or a target level of performance.

BRIEF DESCRIPTION OF THE DRAWINGS

The figures described below depict various aspects of the system and methods disclosed herein, it should be understood that each figure depicts an example of aspects of the present systems and methods.

DETAILED DESCRIPTION

Figure 1:
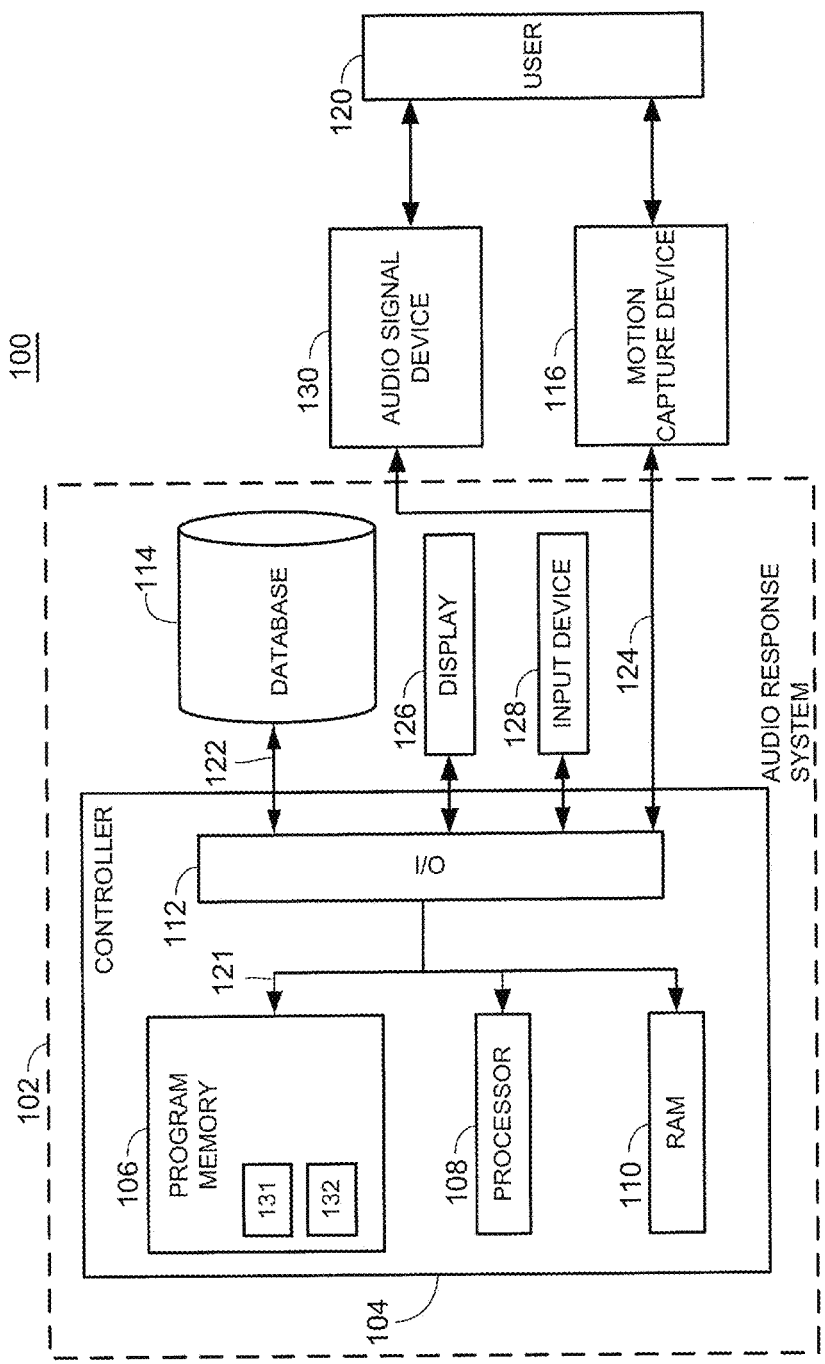
FIG. 1 is a schematic illustration of an example system for audio response that adjusts audio signals in response to changes in sensed kinematic, kinetic, spatial and/or temporal motion of a subject.

FIG. 1 illustrates an audio effects system 100 having various components used in implementing techniques described herein. An audio effects device 102 is coupled to a motion data capture device 116 that collects kinematic, kinetic, spatial and/or temporal motion data for a subject 120 (e.g., a user). In many examples herein, the motion capture device 116 is described as sensing "kinematic motion" data. However, it will be understood that such "kinematic motion" data may be any of kinematic, kinetic, spatial and/or temporal motion data collected by a suitable device. Therefore, references to any of kinematic, kinetic, spatial and/or temporal motion data should be viewed as including, implicitly, references to any other of kinematic, kinetic, spatial and/or temporal motion data. Also, at times herein the term "motion data" will be used as shorthand for any of these various types of data.

The kinematic motion data may represent motion patterns of the subject, such as walking patterns, running patterns, agility patterns, etc. In some examples, the motion patterns involve specific activities, such as predetermined rehabilitation maneuvers (also termed movements) or sports training maneuvers. As used herein, the term "kinematic motion data" typically refers to the data collected from sensors, such as inertial-measurement units, while the term "motion characteristics" refers to a higher-level, qualitative performance trait that can be determined from the kinematic motion data, traits such as gait speed, step width, step width, step length, stance time, gait phase, symmetry of the limbs, inertial motions of the limbs, cadence, path of pressure, path of center of mass, ground reaction force, lower limb or sacral trajectory, trunk orientation, trunk flexion/extension, hip Flexion/extension, knee flexion/extension, foot-floor angle at heel contact, ankle plantarflexion/dorsiflexion, and/or energy cost. In some example implementations, sensors are able to determine and provide such motion characteristic data directly without further processing, in which case the kinematic motion data would itself contain motion characteristic data.

Figure 2:
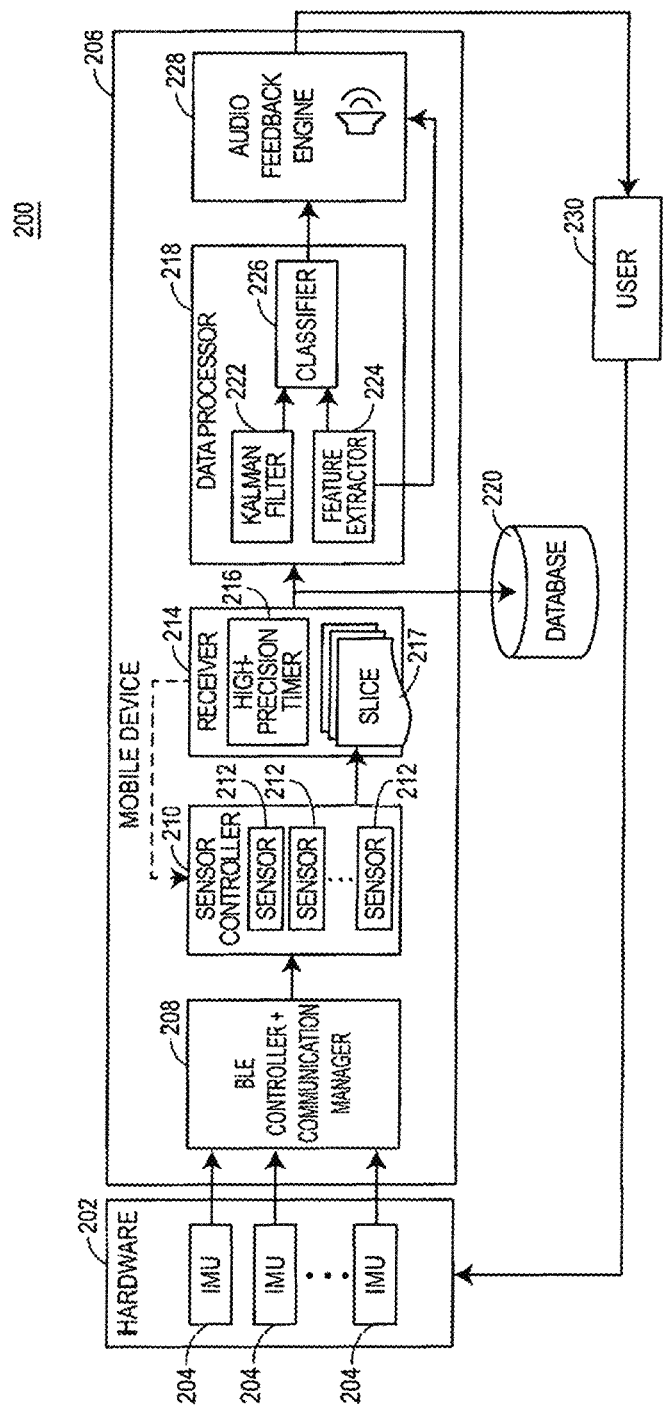
FIG. 2 illustrates a system for kinematic, kinetic, spatial and/or temporal motion data acquisition and audio feedback control, as may be implemented by the system of FIG. 1.

The capture device 116 may be a wearable device, such as a wearable smart device attachable to a person. By way of example, not limitation, the capture device 116 may be a wearable sleeve device that is fitted for use on a person's knee, foot, ankle, leg, torso, waist, arm, shoulder, elbow or wrist containing a sensor for acquiring kinematic motion data. Examples of kinematic motion capture include inertial measurement units, reflective markers for optical systems, microphone systems, infra-red source/sensor systems, magnet/magnetometer systems, or proximity detectors. The capture device 116 may have a stretchable fabric sleeve embedded with one of these kinematic or position estimating sensors, for example. The motion capture device 116 may be a smart watch or other wrist wearable device. The motion capture device 116 may represent a plurality of devices, each with a sensor and each positioned on a different portion of a user's body. Example depictions of the capture device 116 are shown in FIG. 2, as well as in FIGS. 6A and 6B.

The capture device 116 collects and stores motion data on the subject 120, as raw data, processed data, or pre-processed data. That motion data includes data on any number of characteristics, statistics, or derived parameters of kinematic motion.

In some examples, the system 100 is operable in a first mode, called a training mode, where the system 100 collects data and develops audio models, baselines, heuristics, and/or other characteristics that are used to during a second mode, called the performance mode.

In the training mode, the system 100 collects training data, such as baseline data on the kinematic motion, of a person serving as the subject 120. The baseline data represents motion data at a first instance of time, serving as a point of comparison for motion data taken at subsequent instances of time. By way of example, this initial motion data may be collected by having the subject 120 perform a series of specific training maneuvers, such as level ground walking, incline and decline walking, stair ascent and descent, walking on uneven terrain, jogging, running, agility, single-limb stance, jumping, or slaloming, and other ambulatory activities during optimum conditions.

In some examples, instead of data exclusive to the subject 120, training data may include data from a number of subjects compiled together as aggregated training data. In some examples, that aggregated training data is coded with demographic data, such that the system 100 may use demographic-specific subsets of that aggregated data when developing training models for a subject associated with a particular demographic group.

The system 100 includes an audio output device 130 coupled to the subject 120. Under the control of the audio effects device 102, the output device 130 provides audio signals to the subject 120. The audio signals are timed and controlled during collection of the motion data and may be optionally used in a training mode when determining baseline motion performance of the subject. That is, the audio signals are optional during the training mode. The system 100 may collect performance baseline data without providing an audio signal to the subject 120. Or, the system 100 may provide audio signals to the subject 120 and collect motion performance data during audio play, in which collected motion performance data is synchronized with the audio signals.

Whereas the audio signals are optional in the training mode, in the performance mode, the system 100 provides audio signals to the subject 120 and controls audio characteristics of those signals, while measuring motion performance of the subject 120. The system 100 controls these audio characteristics to optimize, in real time, motion performance of the subject 120. That performance optimization may mean increasing motion performance of the subject 120 to reach the baseline performance determined during a training mode. Additionally, performance optimization may mean maintaining performance of the subject 120 if the baseline performance is reached or exceeded. This type of optimization may be particularly useful for a person who has undergone an injury or has compromised performance for other reasons, such as from performance fatigue. In other examples, the audio signals are altered to enhance a person's motion performance beyond a baseline, for example, when training athletes to increase peak performance.

In any event, the motion capture device 116 is communicatively connected to the audio effects device 102 through a wired or wireless link 124. For the former, the capture device 116 may capture and store captured motion data during operation, and connect to the audio effects device 102 through a Universal Serial Bus (USB), IEEE 1394 (Firewire), Ethernet, Inter-Integrated Circuit (I2C), serial peripheral interface (SPI), universal asynchronous receiver/transmitter (UART), or other wired communication protocol connector.

The wireless connection can be achieved using any suitable wireless communication protocol, such as, WiFi, NFC, iBeacon, Bluetooth, Bluetooth Low Energy (BLE), X-Bee, ZigBee, Radio Frequency, infrared, ANT, ANT+, RFID, INSTEON, Wireless USB, Z-Wave, or other personal, body, or near-me area networks.

The audio effects device 102 has a controller 104 operatively connected to a database 114 via a link 122 connected to an input/output (I/O) circuit 112. It should be noted that, while not shown, additional databases could be linked to the controller 104 in a known manner. The controller 104 includes a program memory 106, the processor 108 (may be called a microcontroller or a microprocessor), a random-access memory (RAM) 110, and the input/output (I/O) circuit 112, all of which are interconnected via an address/data bus 121. It should be appreciated that although only one microprocessor 108 is shown, the controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. The link 124 operatively connects the controller 104 to the capture device 116, through the I/O circuit 112.

The program memory 106 and/or the RAM 110 may store various applications (i.e., machine readable instructions) for execution by the microprocessor 108. For example, an operating system 131 may generally control the operation of the audio effects device 102 and provide a user with a digital user interface to the device 102 to implement the processes described herein. The program memory 106 and/or the RAM 110 may also store a variety of subroutines 132 for accessing specific functions of the audio effects device 102. By way of example, the subroutines 132 may include, among other things: a subroutine for providing training mode and performance instructions to the capture device 116; and subroutines, as discussed herein, for collecting kinematic motion data, processing that data, extracting characteristics from that data, determining classifiers for that data, mapping that motion data to smartly-determined audio characteristics, adjusting those audio characteristics and providing them to a subject, measuring for changes in kinematic motion performance of the subject in response to those adjust audio characteristics, and continuing that process continuously and in real time to improve kinematic performance.

For example, collection of data may be performed by one or more inertial measurement unit (MU) sensors in the motion collection device 116. Processing of the collected sensor data may be performed by a data processor, such as a data processor in a mobile device. In the example of a user walking, the system will collect kinematic motion data from sensors worn in a knee sleeve. That kinematic motion data may then be processed with filtering, e.g., to reduce noise, and/or with rotation correction, i.e., to virtually align the sensor with the segment's frame of reference. The motion capture device 116 may extract motion characteristics, such as joint angles, limb velocities, and temporal and spatial parameters of gait from the collected data. A collection of extracted motion characteristics is indicative of a gait deviation. For example, spending extra time on one foot compared to the other (stance time asymmetry) and decreased knee flexion on the injured side could be indicative of pain, weakness or poor balance. Additional motion characteristics such as stride length and/or the timing of events throughout the phases of gait provide motion profiles that will differentiate the cause of a gait deviation. Then, the device 102 may determine the extent of deviation of various motion characteristics, such as the severity or amount of motion deviation. The severity or amount is thus correlated to an audio effect and audio effect change amount that is applied to the audio stream provided to the user. Finally, the motion characteristics are re-measured (continuously, at periodic times, in response to triggers, of after some passage of time) to track the improvement of motion performance or gait. Other example processes to be executed by the subroutines are described herein.

The subroutines 132 may include other subroutines, for example, implementing software keyboard functionality, interfacing with other hardware in the device 102, etc. The program memory 106 and/or the RAM 110 may further store data related to the configuration and/or operation of the audio effects device 102, and/or related to the operation of one or more subroutines 132. For example, the data may be data gathered from the system 100, from data determined, and/or from data calculated by the processor 108, etc.

In addition to the controller 104, the audio effects device 102 may include other hardware resources. The device 102 may also include various types of input/output hardware such as a visual display 126 and input device(s) 128 (e.g., keypad, keyboard, etc.). In an embodiment, the display 126 is touch-sensitive, and may cooperate with a software keyboard routine as one of the software routines 132 to accept user input. It may be advantageous for the audio effects device to communicate with a broader network (not shown) through any of a number of known networking devices and techniques (e.g., through a computer network such as an intranet, the Internet, etc.). For example, the device may be connected to a database of motion information, a database of aggregated kinematic motion data, a database of historical kinematic motion data for a subject, a database of audio performance information, a database of audio signals (music, etc.), a database of demographic data, a database of subject 120 medical history, or other database. In some examples, the disclosed embodiments are used as part of an automated closed loop system audio response system. That the audio effects system may be a stand-alone system. In other examples, the audio effects system is implemented in an existing audio player device, such as portable music player or cellular phone, smartphone, smart watch, fitness monitoring device, or other smart device.

FIG. 2 is a schematic of a system 200 for kinematic motion data acquisition and audio feedback control as may be implemented in an example implementation of the system in FIG. 1. Motion data is captured by a hardware device 202, attached to a user 230, and having a plurality of inertial measurement units 204 (IMUs, e.g., acceleration, gyroscope, and compass heading data) that detect kinematic motion in the user 230. The hardware device 202 may represent one or more motion capture devices located on a person, each with one or more sensors. The IMUs 204 are positioned on the user 230 to detect movement along any of a desired number of degrees of motion. The IMUs 204, for example, may be positioned on a knee sleeve and arranged to detect motion over a Cartesian coordinate system defined by x-, y-, and z-axes. In other examples, the knee sleeve is configured such that the IMUs detect motion of the knee over a spherical coordinate system, defined by r, θ, and φ (see, e.g., FIGS. 6A & 6B). Other IMU configurations will be known to persons skilled in the art. Further, the number of IMUs and their configuration may depend on the type of motion detection device 202 and where that device is positioned on the body.

In the illustrated example, the device 202 is implemented as a wireless communication device, namely a Bluetooth device, e.g., using low energy Bluetooth, although any number of wired or wireless protocols could be used. As such, the device 202 includes one or more processors, one or more memories, and one or more wireless transceiver devices. In the example of multiple motion capture devices forming the device 202, each device may be Bluetooth enabled. The device 202 transmits collected motion data to an audio effects system 200, which may be implemented on a mobile device, such as a smartphone, smart watch, fitness monitoring device, or other mobile device. The system 200 represents executable instructions as may be stored in a program memory, such as the program memory 106, and more specifically in the subroutines 132. In the illustrated example, the collected motion data is initially provided to a Bluetooth Low Energy (BLE) controller and communication manager 208, which performs communication functions such as data packer header stripping and analysis, data packet synchronization, payload analysis, etc.

A sensor controller 210 is coupled to the communication manager 208 for exchanging control signals and sensed signals with the hardware 202, where in the illustrated example, there is a dedicated sensor controller 212 for each of the IMUs 204. The sensor controllers 212 provide control signals instructing the device 202 when to collect motion data and may time those instructions with audio feedback signals. A receiver 214 provides a high precision timer 216 that synchronizes timing of the motion data capture with the output of audio feedback signals to the person, which allows for more accurate signal altering, as discussed further below. A slice circuit 217 is used to select all motion data or certain relevant segments of the motion data; that allows the system 200 to collect and analyze motion data only over certain time windows.

The sliced motion data and/or windowed motion data from the MIA 204 and sensor controllers 212 is provided to a data processor circuit 218 that processes the motion data and to a database 220 that stores the data for historical reference and for access by the data processor circuit 218 during routine. The circuit 218 may continually collect motion data, in real time. Data from IMUS can be rather noisy. In some examples, the motion data may be sliced as simultaneous data across many different data channels, thus identifying an instant in time across all IMUS. In some examples, a short duration of data is sliced for one or more data channels, to identify one or more windows of time. Window data may represent simultaneous events, while in other examples, the window data may be staggered across the IMUs, with some window data having start and stop times that precede those of other window data.

The circuit 218 may reduce noise through standard filtering techniques. The circuit 218, however, specifically optimizes noise reduction over time and optimizes estimates of the motion data by using a Kalman filter module 222. The Kalman filter module 222 includes any combination of a family of filter implementations, including, for example, an indirect Kalman filter, unscented Kalman filter, and extended Kalman filter. The Kalman filter module 222 provides accurate estimates of the x-y-z or r-θ-φ coordinate values by comparing a current state of motion data to a previously stored state of motion data, recursively, optimizing the actual state. Other filters for estimating coordinate values may be used, including a complementary filter, explicit complementary filter, or gradient descent filter.

It is worth noting, the motion data may include many characteristics determined from the x-y-z or r-θ-φ coordinate data. A feature extraction module 224 extracts desired motion characteristics (or features) from the kinematic motion data and provides that data to a classifier module 226, which assesses the kinematic motion data of the subject in response to the feature extraction data and the optimized estimation data from the Kalman filter module 222.

Examples characteristics extracted by the data processing circuit 218, include motion characteristics (or features) such as gait speed, step width, step width, step length, stance time, gait phase, symmetry of the limbs, inertial motions of the limbs, cadence, path of pressure; path of center of mass, ground reaction force, lower limb or sacral trajectory, and/or trunk orientation. Other motion characteristics include trunk flexion/extension, hip Flexion/extension, knee flexion/extension, foot-floor angle at heel contact, ankle plantarflexion/dorsiflexion, and/or energy cost. Yet, other motion characteristics include statistical descriptors, such as mean, range, variance, entropy, correlation, and regularity.

The data processor circuit 218 processes the kinematic motion data and the classification data and generates audio signal instructions that are provided to an audio feedback engine 228 configured to provide audio signals to the user 230. The instructions are designed to alter audio signals in response to the motion assessment data, in order to optimize motion performance of the user. For example, the classifier 226 may include a perceptual mapping module (or a portion thereof) that maps extracted motion characteristics to one or more characteristics of the audio signal stored in the audio feedback engine 228. From this mapping, the engine 228, through its audio effects module, adjusts characteristics of the mapped audio characteristics based on the changes in motion data (e.g., deviation values) of the extracted motion data. The resulting changed audio signal is provided to the user 230 through headphones or other speakers.

For example, in assessing a user's walk, data on certain sets of motion characteristics are captured through the use of the hardware 202. The particular motion characteristics assessed (and thus the particular kinematic motion data from the sensors) would be those associated with a "Best Walk" of the user and are used as a baseline during a performance mode testing. Collected motion characteristic data is stored in the database 220. During a home use, the hardware 202 collects the same motion characteristics from the user. The classifier 226 determines the difference values between the home use values and training (baseline) mode values. The classifier 226 rates the motion characteristics based on these difference values, e.g., a gait deviation percentage (%), In this manner, the system determines whether the motion characteristics are substantively equal to or different from the stored motion characteristics from the database. Depending on the type of deviation, as determined by the classifier 226, the feature extractor 224 selects a specific audio effect to alter. For example, if reduced knee flexion is detected, then low-pass filtering may be applied to the music signal. The severity of the audio feedback, e.g., the severity of the low-pass filtering, is graded based on the severity of the gait deviation.

The engine 228 is able to adjust audio characteristics by performing modulations to any linear or nonlinear filter that impacts signal amplitude, frequency, or phase. The adjustable mapped audio characteristics may include, but are not limited to: amplitude modulation, frequency modulation, distortion, bitcrushing, chorus, ducking, frequency filtering (high-pass filtering, a band-pass filtering, a low-shelf filtering, a high-shelf filtering, or a band-stop filtering), spatialization, localization, panning, reverb, echo, compression, expanding, phasing, flanging, gating, vocoding, pitch-shifting and/or delay of the audio signal.

In this way, the data processor circuit 218 working in conjunction with the audio feedback engine 228 provides a learning module that assesses kinematic motion data of the user 230, as that user moves while listening to audio signals. The learning module can continually adjust real time) these audio signals based on assessments of that user's motion, with the purpose of optimizing that motion. That motion optimization may be achieved by optimizing the audio signal provided to the user 230 as the user's motion improves. For example, if the audio signal is a song or voice instruction, then as the user's motion improves in performance (e.g., as the user's gait improves to a desired gait), the song or voice instruction changes from a distorted version thereof to an increasingly undistorted version thereof. This instantaneous feedback allows users to more quickly and more accurately reach their motion goals, whether for rehabilitation purposes or for training purposes. The audio feedback engine 228 is able to adjust the values of each of the set of mapped characteristics based on the output of the kinematic classifier 226, which could be a neural network, Bayesian or other probabilistic classifier, support vector machine, linear/quadratic discriminant analysis machine, clustering algorithm, deep learning method, and/or an ensemble method. The engine 228 alters the audio characteristics to be adjusted in response to motion data changes. That is, the engine 228 adjusts audio characteristics in a real time continuous manner, and the engine 228 may adjust which characteristics are adjusted (and by how much), to obtain optimized motion performance of the subject.

Figure 3:
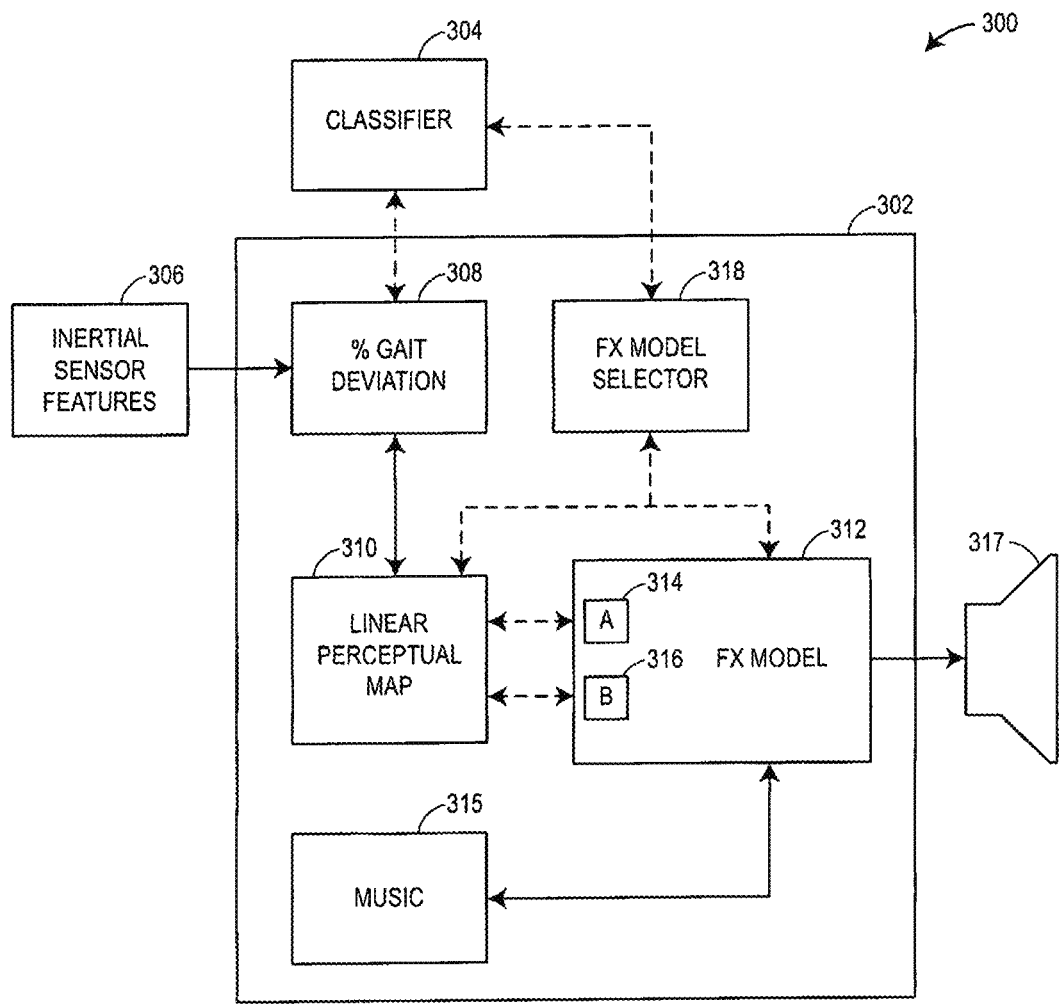
FIG. 3 illustrates a controller that performs perceptual mapping and adjusts audio signal effects in response to optimize kinematic, kinetic, spatial and/or temporal motion of a subject.

FIG. 3 illustrates an example controller 300, which is an implementation of the audio feedback engine 228 shown in FIG. 2. The controller 300 includes an audio feedback engine 302 that receives data from a motion data classifier 304 that identifies different kinematic, kinetic, spatial and/or temporal motion activities of a subject (not shown). The classifier 304 provides categories of performance (e.g., any motion data is categorized is one of a few categories: sub-par performance, acceptable performance, improvable performance, peak performance) while the inertial measurement sensor characteristics 306 provide details of the performance within the category. A sensor module 306 extracts kinematic, kinetic, spatial and/or temporal motion characteristics (i.e., motion characteristics) and provides that motion characteristic data to the controller 300. From there, in the illustrated example, performance is measured by a percentage change of normative gait values, e.g., deviation from a desired normal gait value. That percentage deviation is determined by the module 308, which passes that information to a linear perceptual mapping module 310 to map the kinematic, kinetic, spatial and/or temporal data to audio effects characteristics stored in an audio effects module 312. In the illustrated example, the mapping module 310 maps the percentage gait deviation to audio characteristic parameters A (314) and B (316). The effects module 312 receives music stored in a music memory 315 and applies musical effects (the changes in A 314 and B 316) to that music, which is then played on a speaker 317.

An audio effects selector module 318 is also coupled to the effects module 312. The selector module 318 instantiates an auditory effect filter based on classification of the category of kinematic, kinetic, spatial and/or temporal performance obtained from the classifier 304, coupled to receive extracted characteristics from the module 306. The classifier 304 may automatically determine classifications, such as, for example, sub-par performance, acceptable performance, improvable performance, or peak performance. For example, each performance category may correspond to a specific (but arbitrarily assigned) audio effect, or to no audio effect if no deviation from peak performance was detected. The classification is made based on observation of derived characteristics of the kinematic, kinetic, spatial and/or temporal data being collected. As discussed in other examples herein, classification may be performed by an artificial neural network fed with motion feature data from the characteristics module 306. In other examples, the classifier 304 may employ a naïve Bayesian classifier, support vector machines, linear discriminant analysis, quadratic discriminant analysis, clustering algorithm (such as K-nearest neighbors or K-means), deep learning method (including deep neural networks, convolutional neural networks, or deep belief networks), ensemble methods (including boosting, bootstrapping, and expert systems strategies), combinations thereof, or other techniques. The learning performed by the classifier 304 is used to classify the subject's kinematic, kinetic, spatial and/or temporal performance. In some examples, the classifier 304 may further determine with motion data characteristics are most correlative to get deviation and then instruct module 306 to extract those characteristics or only those characteristics.

After performance category classification, the audio effect is applied to music playback. The linear perceptual mapping module 310 maps parameters of the audio effects characteristics (e.g., A 314 and B 316) to derived characteristics of the kinematic, kinetic, spatial and/or temporal data from the module 306. The module 310 may perform that mapping in a number of ways. (1-to-1): Mapping of any one derived kinematic, kinetic, spatial and/or temporal feature directly to the depth of application of the audio effects characteristic. (Many-to-1): Mapping of any combination of derived characteristics directly to depth of application of the audio effects characteristic through use of a linear discriminant model or quadratic discriminant model, etc. to obtain the combination of characteristics that maximize the amount of information transferable to the subject within the bounds of human perception and tolerance for abrasive noises. Alternatives to linear or quadratic discriminant models include: classification trees, auto encoder neural network, principal or independent component analysis, factor analysis, non-negative matrix factorization, canonical correlation. In this way, the perceptual mapping module 310 and the audio effects module 312 are configured to allow for automated smart adjusting of the audio characteristics based on which characteristics are determined will achieve the more effective improvements in kinematic, kinetic, spatial and/or temporal motion performance. If a user is displaying particular types of motion problems (e.g., characteristics, such as gait speed, step width, ground reaction force, etc.) then the module 310 smartly maps those problems to audio effects specifically determined to alter those motions problems. For other motion problems, then other audio effects would be altered. These mappings may be determined empirically. The mappings may be user specific or they may be determined for aggregated data across user populations. The mappings may be determined during training modes or during performance modes. Example audio effects adjustments are described herein, and include amplitude modulation, distortion, bass-cut filtering, frequency modulation, spatialization (e.g., stereo to mono), localization (e.g., head related transfer functions), reverb, echo, and delay, high-pass filtering (simulates hearing loss), band-pass filtering (simulates a telephone), lossy compression (simulates audio over internet), phasing or flanging.

The performance mode may be implemented in a number of different contexts, for example, as a part of a rehabilitation process or sports performance enhancement process.

Figure 4:
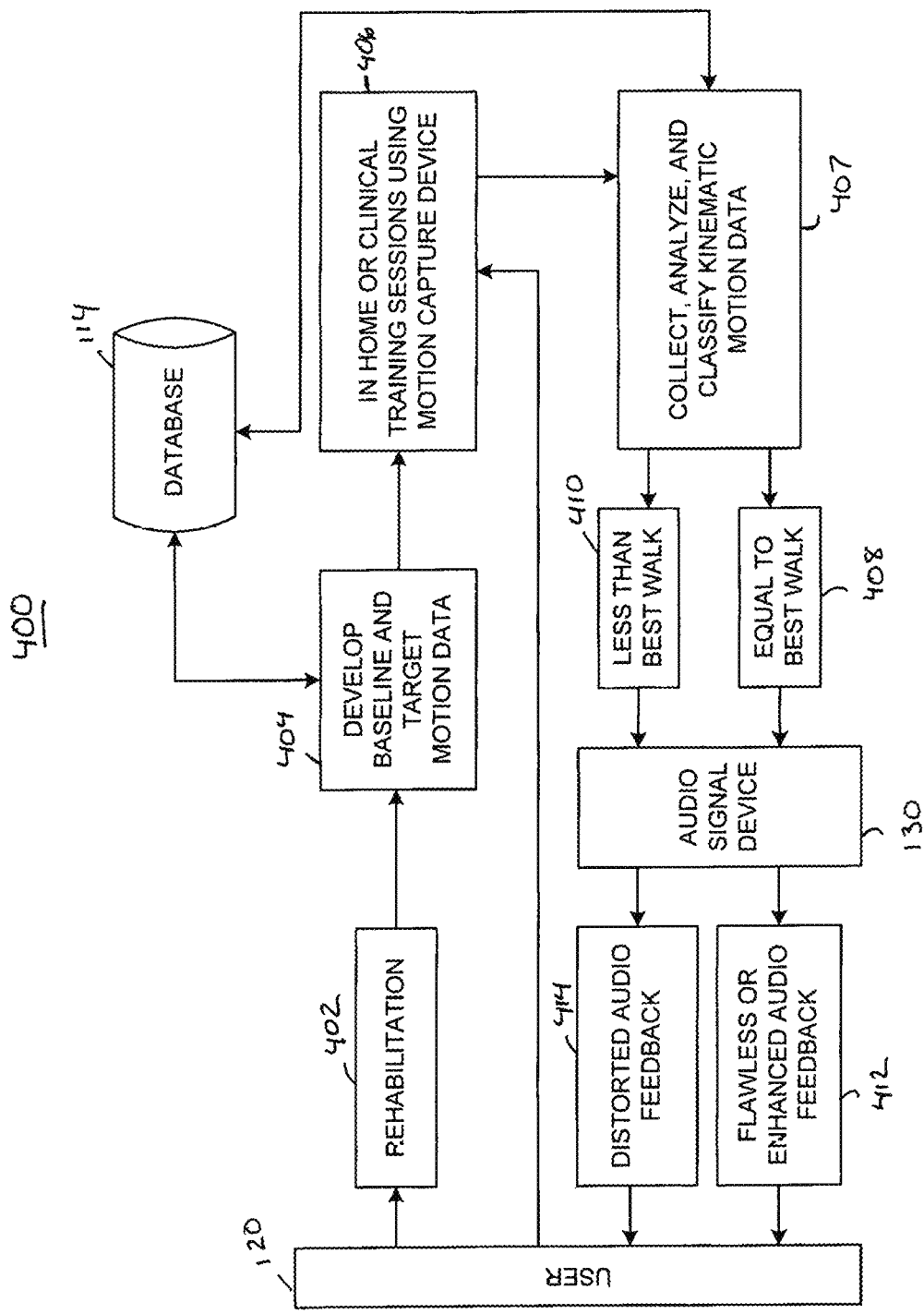
FIG. 4 illustrates an example rehabilitation process for a performance mode implemented by the system of FIG. 1.

FIG. 4 illustrates a rehabilitation process 400 as may be implemented using the system of FIG. 1. Assume the patient 120 user had a recent knee surgery and demonstrated limited knee flexion and extension, the user 120 would attend rehabilitation training 402, such as physical therapy. At the conclusion of the physical therapy treatment, the user 120 may have increased their knee motion when compared to the beginning of treatment.

At the conclusion of the rehab training 402, using a motion capture device, baseline and/or target data (404) is obtained for a patient, e.g., to identify the target knee flexion and extension angle for an optimum walk.

The data collected on at process 404 may be the "Best Walk" for the patient at the point in time during rehabilitation. The "Best Walk" may be determined from a single walk or from having the user 120 go through a series of walks and the best walk is determined from those. In the latter example, which walk is the "best" walk may be determined electronically, e.g., through a repeated number of walking routines each having stored data that is compared against other stored walking data, either collected from that patient during the tests, from that patient prior to the tests, from a sampling of a other healthy patients, with a similar walking type, or through comparison against other historical data.

This baseline and/or target data is stored (404), and the user 120 is provided with the motion capture device 116 for measuring the patient's walking after rehabilitation. The user 120 may go through a series of walks or a single walk. In the illustrated example, the user 120 is provided with the motion capture device 116 for use on their own, in home environments or in supervised clinical settings 406.

Figure 6A:
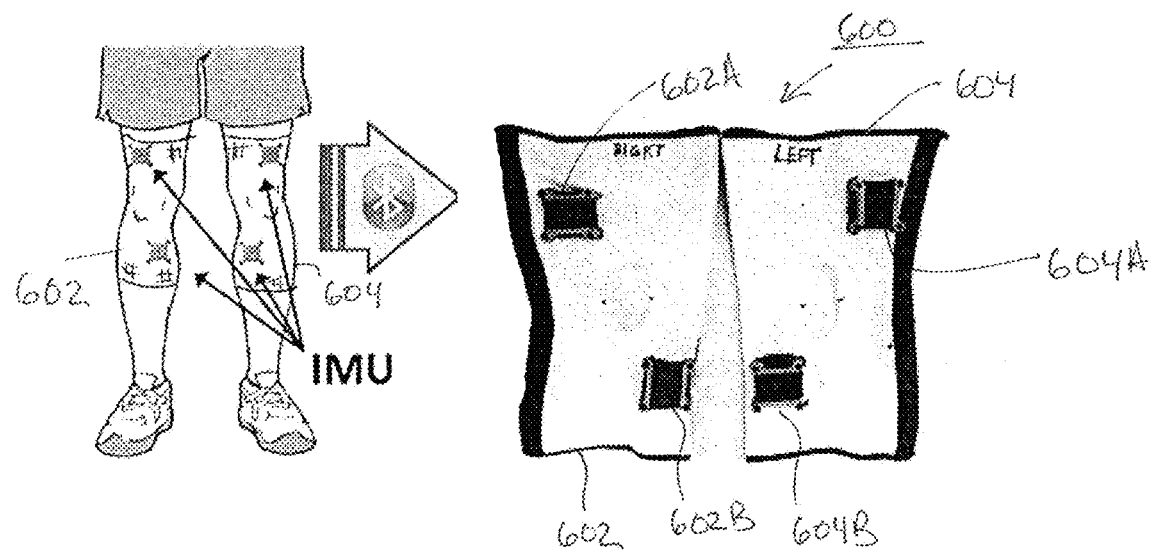
FIG. 6A illustrates an example measurement sleeve containing multiple sensors for use in the system of FIG. 1.

An example motion capture device 600 is shown in FIG. 6A, and has two sleeves 602 and 604, one for each knee, and each having two IMU sensor 602A/602B and 604A/604B, respectively. In the illustrated example, the sleeves 602 and 604 deploy IMU sensors on front portions thereof, i.e., at an anterior position of the leg.

To assess movement, the user 120 walks at their comfortable walking speed, while motion characteristics (e.g., gait speed, step width, step length, stance time, gait phase, limb symmetry, knee flexion, and/or extension angles, etc.) are determined and stored in the database 114.

During the performance mode, at 406 with the user 120 wearing the motion capture device 116, kinematic motion data is collected. Data may be collected continuously, periodically, at programmed times, and/or in response to triggering events, such as the user using the input device 128 to instruct the device 116 to begin recording or having the device 116 begin recording if the sensor data shows a change in the kinematic motion data above a threshold change amount.

At a process 407, implemented on the computer system 100, the data is collected from the process 406, classified as needed, and compared with the baseline data and/or target data from the process 404. Alternatively, the data may be compared against data collected during the last physical therapy session, for patients having ongoing rehabilitation sessions.

In comparing the collected data to the baseline data, the system 100 may compare any of the kinematic motion data individually and/or any composites thereof. In some examples, the computer system 100 compares each data collected on a data-to-data basis and determines if the new data is within a predetermined range to the baseline data, that identifies whether the user 120 is walking equivalent to or better than their best walk 408 or below their best walk 410.

At the process 407, if the computer system 100 determines that the user is walking within a knee range of motion equal to or better than their baseline data (408), the feedback process 400 will provide one or a combination of positive feedback responses such as flawless audio music (412) that is played correctly or a music effect that enhances the listening experience, such as a "bass boost", by the audio device 130.

Conversely, if the process 407 determines that the knee range of motion negatively deviates from the baseline data (less than "Best Walk," 410) then the feedback process 400 will provide one or a combination of corrective audio feedback responses, such as distorted audio music (414) that is played inaccurately. Because the process may run continuously, corrective feedback can become positive feedback once the user regains their "Best Walk."

The classifier process 407, thus, will detect if the user deviated from their last recorded Best Walk, which may be recorded at the clinic or in home by the user. The audio feedback system will provide feedback if the user deviates from their Best Walk. The reasons for the deviation may be many, and the audio feedback system may be adapted to thereby address any or all of these, e.g., lack of concentration, the user forgets to walk correctly, the user becomes fatigued, the user acquires a habit, or any other reason for deviation. The process of capturing the user's Best Walk and improving the user's gait can be repeated throughout the rehabilitation process until the rehabilitation goals for gait are achieved.

In the example of FIG. 4, the feedback process 400 is based on a user's Best Walk, because; 1) people walk differently, 2) during rehabilitation it may take a person an undetermined amount of time to restore their normal gait, and 3) with some diagnoses a "normal gait" may never be accomplished, for examples people with amputations, Parkinson's disease or stroke. Other example rehabilitation activities will be apparent, including those for a patient's legs, arms, fingers, wrists, back, etc.

Figure 5:
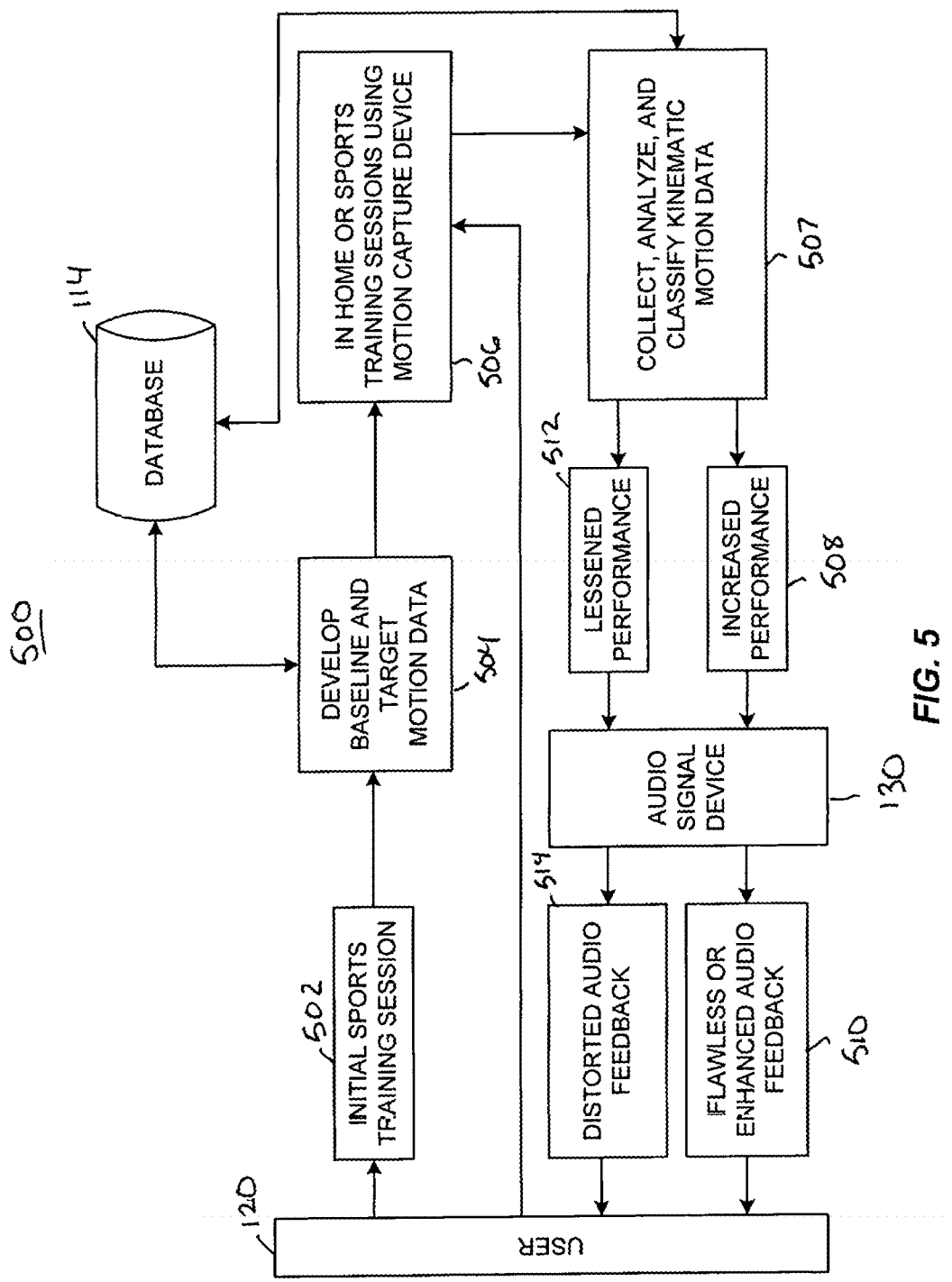
FIG. 5 illustrates an example sports performance enhancement process for a performance mode implemented by the system of FIG. 1.

FIG. 5 illustrates a similar process to the rehabilitation process 400 but shows a performance enhancement process 500, with similar reference numerals to those of FIG. 4, but in a 500 series, and performing similar features, but wherein in the illustrated example the collected, classified, and compared data is sports specific kinematic motion data. It will be noted that any number of kinematic motion data (and corresponding motion characteristics) may be collected, including gait speed, step width, step length, stance time, gait phase, symmetry of the limbs, inertial motions of the limbs, cadence, path of pressure, path of center of mass, ground reaction force, lower limb or sacral trajectory, and/or trunk orientation. The particular data collected, classified, and compared may vary depending on the activity, the sport the user is training for, and/or the particular movement the user desires to improve.

For example, if the user 120 wants to improve side-to-side mobility, the motion capture device 116 would be worn and as the user is moved rapidly from side-to-side during an initial training session 502. Initial baseline and/or target kinematic motion data is collected and stored in the database 114 (504). The user 120 goes through training sessions 506 to improve the side-to-side movements, and the motion capture device 116 records kinematic motion data which is then provided to a data collection, classification, and comparison process 507, similar to the process 407.

As the user achieves greater symmetry of knee motion during the side-to-side training, the process 407 determines that the motion characteristic performance (indicative of side-to-side movement) is increasing (or equal) 508, in which case the audio signal device 130 is instructed to provide positive audio feedback 510, i.e., with lesser to no distortion in the music and, in some examples, adding audio signal enhancements, such as, bass boosting, increasing tempo, etc.

As with the process 407, the process 507 may assess the amount of motion characteristic improvement and provide a corresponding amount of positive audio feedback 510, where the amount of positive audio feedback changes depending on the amount of performance improvement.

In some examples, the type of positive audio feedback (e.g., bass-boost, tempo, etc.) is determined by the computer system, e.g., through mapping. While in other examples, the user may provide an input to the computer system selecting the desired positive/negative audio feedback type.

Correspondingly, if the process 507 determines that the user 120 is performing below a desired performance level 512, then the audio signal device 130 is instructed to provide negative audio feedback 514, such as distorted audio, that is distorted by an amount depending on how far below the desired performance level the user is at.

In FIG. 6A, the motion capture device 600 includes the two sleeves 602 and 604, one for each knee, and each having the two IMU sensor 602A/602B and 604A/604B, respectively.

Figure 6B:
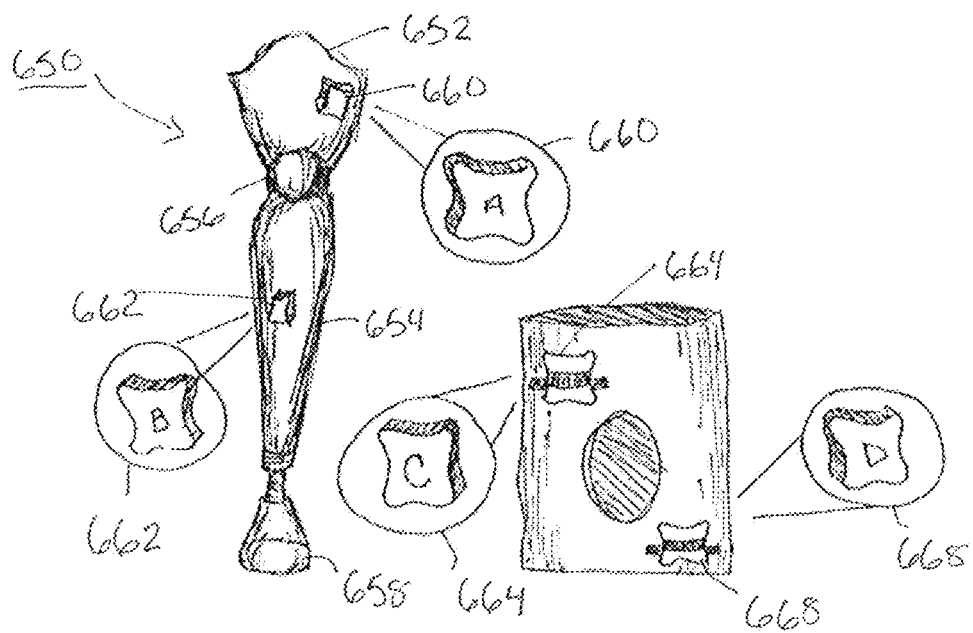
FIG. 6B illustrates an example prosthesis with multiple sensors as may be used in the system of FIG. 1.

FIG. 6B illustrates an example motion capture device 650 in the form of a prosthesis, specifically a leg prosthesis 651, having a socket portion 652 and a lower portion (pylon, shank, etc.) 654 connected by a knee joint 656. A foot 658 is connected to the end of the lower portion 654 opposite the knee joint 656. In the illustrated example, four IMU sensors are mounted to the prosthesis 651. Sensors 660 and 662 are mounted to a front end (anterior) of the prosthesis 651 on the socket portion 652 and the lower portion 654, respectively. Two additional sensors, 664 and 668, are mounted to the rear (posterior) side of the socket portion 652. The particular sensor locations may vary. Furthermore, the sensor positions may be selected to optimize particular types of rehabilitation or performance enhancement measurements. Further still, in some examples, in either configuration of FIG. 6A or 6B, the sensors may be adjustably mounted to be repositioned.

Adjustability may be achieved using a Velcro attachment, slotted track attachment, slotted pocket, strap adjustment allowing the sensors to move along the track, etc., for example.

Figure 6C:
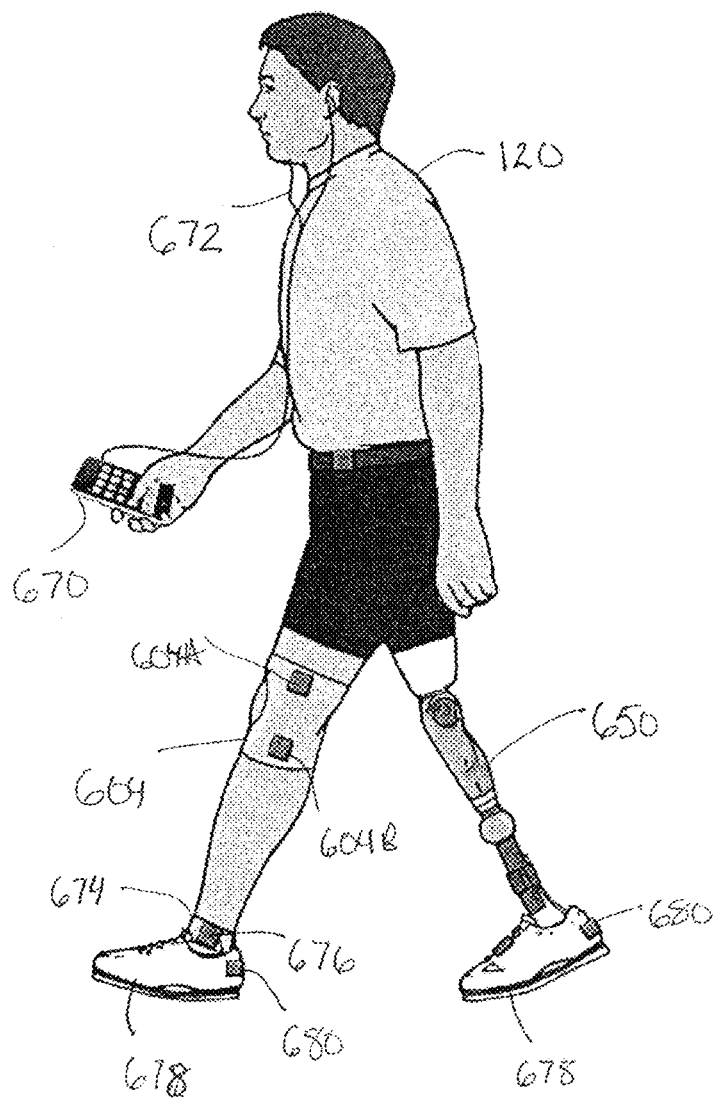
FIG. 6C illustrates an example user having multiple capture devices.

FIG. 6C illustrates an example user 120 with a mobile device 670, e.g., a smartphone, implementing the processes herein (e.g., the system 100 of FIG. 1 or the mobile device 206 of FIG. 2). The mobile device 670 is connected to headphone speakers 672 that provide the audio feedback signals to the user 120. The user 120 is wearing the knee sleeve 604, with the IMUs 604A and 604B positioned laterally to the knee (other IMUs may be used on the sleeve but are not shown). The user 120 is also wearing the prosthesis 650. Optionally, the user 120 is wearing an ankle sleeve 674 with an IMU 676 and a pair of shoes 678 each having an IMU 680. In the illustrated example, each of these IMUs are individually wirelessly enabled to communicate sensed motion data to the mobile device 670, which then assesses that sensed data in accordance with the examples herein.

An example application performance enhancement follows. The users execute software on their computer, handheld device, smartphone, tablet PC, etc. The user selects a performance activity to improve upon, from among a list of performance activities provided to the user. Such performance activities may be rehabilitation activities or sports performance enhancement activities, for example. In some examples, a user first selects whether they want a rehabilitation activity or a sports performance related activity, after which a listing of corresponding training activities are provided to the user for selection. The type of performance activities may be grouped in another ways, instead of by rehabilitation or sports performance, Or the performance activities may not be grouped at all, but rather just listed for selection.

Upon selection of a performance activity, the computer system configures itself to measure those motion characteristics corresponding to the performance activity. Any device pairing protocols are performed, for example, wireless pairing between the sensor device, e.g., a knee sleeve (or brace) with IMU sensors, and an audio signal device which may include wireless headphones or loud speakers.

For example, if a user wants to improve their speed during walks, the user selects using an input device, "walking" from among a displayed list of performance activities. The computer system calls up the necessary protocols for measuring "walking" performance. When the system is ready it may provide a visual indication to the user, after which 1) the user walks at the desired fast speed walk wearing the motion capture device, while the computer system collects the motion characteristics and stores the data in the database.

The computer system may first instruct the user to enter a training mode, where the system determines a baseline for the user's performance. For example, the user may be instructed to move at a "Current Walking Speed," which may be used as a baseline. Alternatively, in other examples, the user may be instructed to walk at a "Target Walking Speed" for that individual at the point in time during training. The "Target Walking Speed" may be the final desired walking speed. A user may be able to sustain that target speed for a brief period of time, while the system seeks to help the user maintain that walking speed for greater distances or for great amounts of time. In the training mode, the computer system may or may not play music or audio signals to the user.

Figure 7:
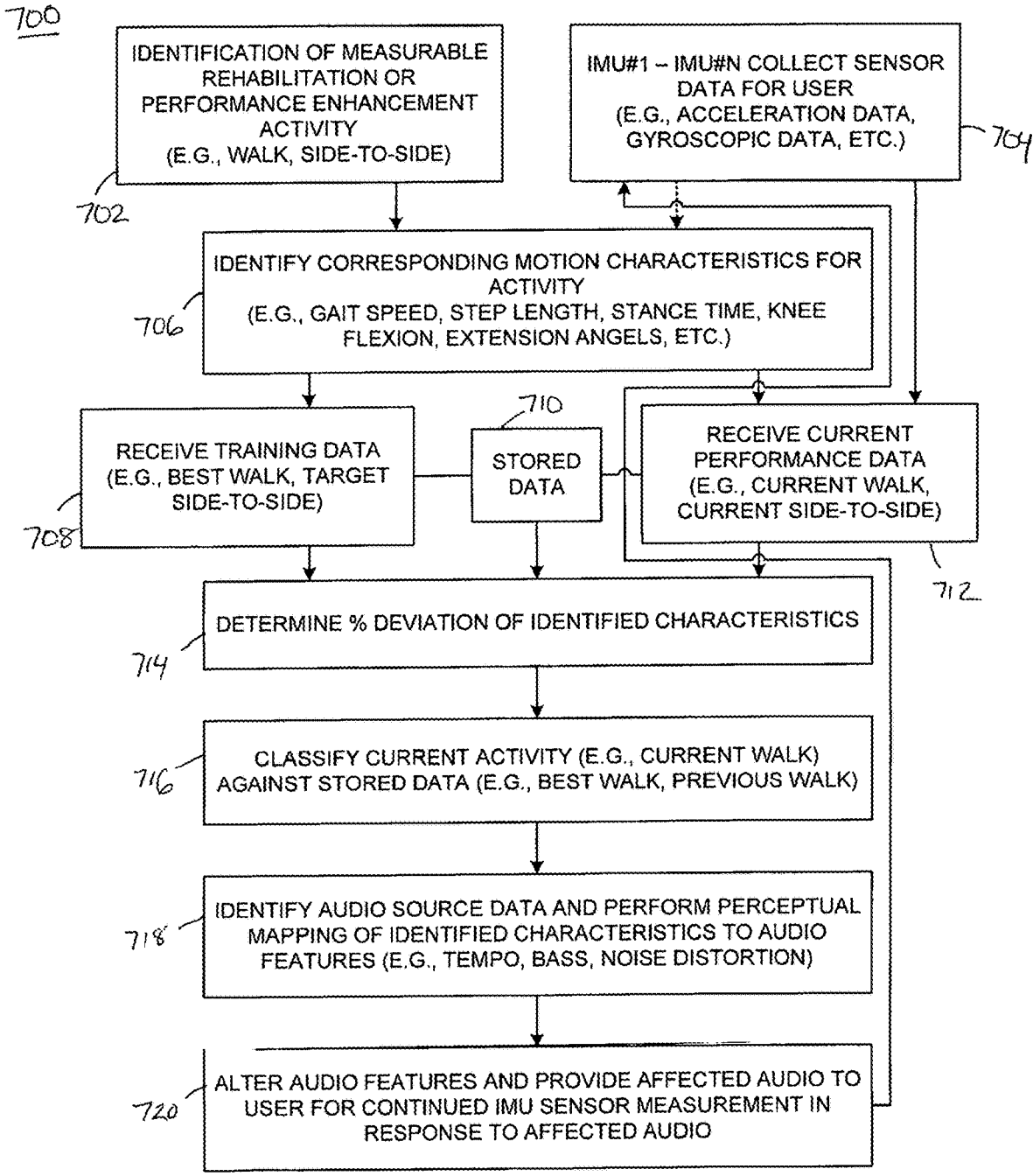
FIG. 7 illustrates a process that may be implemented in accordance with t system of FIG. 1.

FIG. 7 illustrates an example process 700. Initially, at 702, a user identifies a performance activity to be assessed, such as a sports performance activity like side-to-side mobility or a rehabilitation activity such as walking. The process 700 collects sensor data (704) from a plurality of IMUs, $IMU_1 \ldots IMU_N$, found in one or more motion capture devices. During the training mode, the data from steps 702 and 704 is provided to a step 706, in which the system identifies the corresponding motion characteristics for the particularly activity. Those motion characteristics may be such things as gait speed, step length, stance time, knee flexion, extension angles, etc., which the system determines from kinematic motion data collected by the IMU sensors. By way of example, to assess side-to-side mobility, the system may need to assess multiple motion characteristics: step length, step width, symmetry of the legs, inertial motions of the legs, path of pressure, path of center of mass, ground reaction force, lower limb or sacral trajectory, trunk orientation, and hip Flexion/extension. Which motion characteristics correspond to a given selected activity may be determined by the system accessing a lookup table of stored correlations. That lookup table may store correlations for each selective performance activity. Furthermore, that lookup table may be store different levels of correlations, from simplified correlations that look at few motion characteristics to more complex correlations that look at large numbers of motion characteristics.

With the desired motion characteristics determined, during the training mode, training data is collected at 708, where the training data may simply by the collected kinematic motion data from the IMUs and corresponding motion characteristics determined from that motion data. This data may then be stored for future reference at 710. By contrast, during the performance mode, the process 700 collects current motion characteristic data at 712, such as IMU data collected during a current walk performance or current side-to-side performance.

At 714, the system determines an amount of deviation of the current data from 712 against the stored target data of 710.

At 716, the system takes the amount of deviation and applies a rules classification to assess the current motion characteristic performance against the training motion characteristic performance, against the most recently collected motion characteristic performance, against the best previously stored motion characteristic performance, or against any other determined target motion characteristic performance.

The rules classification may include identifying whether a percent deviation is positive or negative and the amount of the percent deviation and assigning a classification accordingly. In some examples, the rules classification is a composite assessment of all identified motion characteristics from the process 706. The rules classification may result from first weighting certain motion characteristics higher or lower in comparison to other motion characteristics, when making such composite assessments. Certain motion characteristics may be more correlative than others to performance in side-to-side mobility, for example. The rules classification may be stored in a rules data structure that is accessed and executed by the system. For example, that data structure may have one or more entries each with a header field identifying the type of classification and at leak one or more data fields with numerical values indicating the classification. The data structure may have entries for each motion characteristic being classified. In some examples, the data structure includes an entry for each kinematic motion data, when that data is also separately classified.

With the motion characteristics classified, at 716, the system determines the classification of the performance activity itself, e.g., lowered side-to-side mobility, same as previous side-to-side mobility, increased side-to-side mobility, or at target side-to-side mobility.

With the performance activity classified, the system identifies, at 718, the audio source data (music, tones, etc.) and performs a perceptual mapping of the identified motion characteristics to particular audio features, such as panning, tempo, bass-boost, distortion, etc. The mapping may be achieved by accessing a lookup table associated various controllable audio features to various motion characteristics and/or to underlying kinematic motion data. In other examples, a user may be able to select which audio features are to be affected. Furthermore, the mapping may include determining the amount of change to be applied to the audio feature.

In this way the type of audio feature and the amount of change may be correlated to particular movements that the user needs to improve.

At 720, the system alters the identified audio features and provides the affected audio to the user who continues to perform the activity in response to the affected audio and the process 700 returns to 704 for updating the collected data and repeating the process.

With these techniques, different performance benchmarks and performance goals may be used. By way of example, performance enhancement can include, improving speed of motion, mimicking motion of an elite athlete, increasing speed or timing with sports related agility maneuvers, or improving the ability to pace an athlete to prevent early fatigue.

In the examples of FIGS. 4 and 5, and in any of the examples herein, the user 120 may be provided with a visual feedback in addition to the audio feedback. Such visual feedback can be provided by a portable, or mobile, display such as a smartphone or tablet, or through an external display connected to the computer system through a networked connection, such as with a network display monitor at sport facility.

The computer system 100, for example, may display motion characteristic information to a user, e.g., listing numerical values for current and baseline characteristics, such as gait speed, step width, step length, etc. In some example, the computer system 100 may use color coding to indicate what ranges the values are in, e.g., different color codes for being below, at, or above, a baseline value metric.

In some examples, the computer system 100 may create graphics that are displayed indicating the performance levels of users. The graphics may be stylized, such as using abstract shapes or avatars representing the users. The graphics may be realistic or pseudo realistic, such as using a depiction of a user performing a motion, or overlaying graphics on real-time video data of a user. For example, a digital image of a three dimensional character walking, performing side-to-side mobility drills, or other motions, may be provided on a display with an indication of how the user is performing against a baseline or target.

In addition to depicting motion characteristic information in real time, the computer system 100 may display graphical representations of the audio feedback. Such a representation could be used to provide a graphical display of music that changes with changes in the performance of the user. Graphical display changes can result from audio feedback induced distortion as well as from audio feedback induced sound improvement.

Further still, the computer system 100 may display data for a single user or multiple users simultaneously for comparison purposes. Moreover, numerical values may be simultaneously displayed for multiple motion characteristics. Moreover, graphs, instantaneous visual characters or animation characteristics would be applied.

As shown, we have developed a system capable of providing an audio feedback, such as through a continuously variable auditory adjustment on musical effects. This process is a type of sonification, where different information is conveyed by mapping some parameter of kinematic, kinetic, spatial and/or temporal motion to some property of auditory effect. With the present techniques, feedback is used to modify (or affect) sound, particularly music, and particularly using specified low level audio characteristics, such as including amplitude modulation, distortion, and filtering, providing a closed loop system of auditory bio-feedback kinematic, kinetic, spatial and/or temporal motion enhancement.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. For example, references and illustrates herein to a "motion capture device," motion capturing hardware device, and the like, include references to multiple ones of these devices as may be used attached to and/or separately spaced from a user. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current

What is claimed:

1. A system to modify an audio signal in response to changes in motion patterns of a wearer of a leg prosthesis, the system comprising:
   the leg prosthesis comprising a socket portion and a lower portion connected by a knee joint, the leg prosthesis further comprising at least one sensor;
   a memory associating a plurality of performance activities with a plurality of motion characteristics and a plurality of controllable audio features, wherein a particular performance activity of the plurality of performance activities is associated with a particular set of motion characteristics of the plurality of motion characteristics and a particular set of controllable audio features of the plurality of controllable audio features; and one or more processors configured to:
receive the audio signal from a source, wherein the source stores the audio signal,
identify a performance of a performance activity for assessment,
consult the memory to identify a first set of motion characteristics and a first set of controllable audio features associated with the performance of the performance activity,
receive sensor motion data from the at least one sensor,
determine a plurality of measurements for the first set of motion characteristics based on the sensor motion data;
determine a deviation value and deviation type based on differences between the plurality of measurements and a corresponding plurality of user-specific target measurements, wherein the corresponding plurality of user-specific target measurements are generated based at least in part on measurements associated with a prior performance of the performance activity by the wearer;
based at least in part on a determination that the deviation value is greater than a first deviation threshold and less than a second deviation threshold, modify the received audio signal by adjusting at least one controllable audio feature of the first set of controllable audio features by a first amount, wherein the at least one controllable audio feature is based at least in part on the deviation type; and
based at least in part on a determination that deviation value is greater than the second deviation threshold, modify the received audio signal by adjusting the at least one controllable audio feature of the first set of controllable audio features by a second amount, and wherein the second deviation threshold is greater than the first deviation threshold the second amount is greater than the first amount.

2. The system of claim 1, wherein the at least one controllable audio feature of the first set of controllable audio features corresponds to at least one of amplitude modulation, frequency modulation, distortion, bitcrushing, chorus, ducking, frequency filtering, spatialization, localization, panning, reverb, echo, compression, expanding, phasing, pitch-shifting, flanging, gating, vocoding, or delay.

3. The system of claim 2, wherein the frequency filtering corresponds to at least one of a high-pass filtering, a bass-cut filtering, a band-pass filtering, a low-shelf filtering, a high-shelf filtering, or a band-stop filtering.

4. The system of claim 1, wherein the audio signal includes music, wherein the modified audio signal becomes increasingly unmodified relative to the received audio signal as the deviation value approaches zero.

5. The system of claim 1, wherein the memory associates only one motion characteristic with each of the plurality of controllable audio features.

6. The system of claim 1, wherein the memory associates more than one motion characteristic with each of the plurality of controllable audio features.

7. The system of claim 1, wherein the at least one controllable audio feature of the first set of controllable audio features comprises at least two controllable audio features.

8. The system of claim 1, wherein the first set of motion characteristics comprises at least two different motion characteristics.

9. The system of claim 1, wherein the first set of motion characteristics comprises at least three different motion characteristics.

10. The system of claim 1, wherein the first set of motion characteristics comprises at least one of gait speed, step width, step length, stance time, gait phase, symmetry of limbs, inertial motions of the limbs, cadence, path of pressure, path of center of mass, ground reaction force, lower limb trajectory, trunk orientation, trunk flexion, trunk extension, hip flexion, hip extension, knee flexion, knee extension, foot-floor angle at heel contact, ankle plantarflexion, ankle dorsiflexion, or energy expenditure.

11. The system of claim 1, wherein the plurality of measurements is a second plurality of measurements, wherein the sensor motion data is second sensor motion data, wherein the performance of the performance activity is a second performance of the performance activity, wherein the prior performance of the performance activity is a first performance of the performance activity, wherein the measurements associated with a prior performance of the performance activity is a first plurality of measurements, and wherein the one or more processors are configured to:
receive first sensor motion data associated with the first performance of the performance activity by the wearer;
determine the first plurality of measurements for the first set of motion characteristics based on the first sensor motion data, and
generate the first deviation threshold and the second deviation threshold using the first plurality of measurements, wherein the first deviation threshold and the second deviation threshold correspond to the first performance of the performance activity by the wearer.

12. The system of claim 1, wherein the performance of the performance activity is a second performance of the performance activity by the wearer, wherein the prior performance of the performance activity is a first performance of the performance activity, and wherein the one or more processors are configured to:
generate the first deviation threshold and the second deviation threshold using the plurality of prior measurements associated with the first performance of the performance activity by the wearer.

13. The system of claim 1,
wherein based at least in part on a determination that the deviation value exceeds at least the first deviation threshold, the one or more processors modify the received audio signal to provide negative audio feedback, wherein the negative audio feedback corresponds to a distortion of the received audio signal, and
wherein based at least in part on a determination that the deviation value does not exceed the first deviation threshold, the one or more processors modify the received audio signal by a third amount to provide positive audio feedback, wherein the positive audio feedback includes at least one of a bass boost or increase in tempo.

14. The system of claim 1, wherein the plurality of measurements is automatically classified into a performance category, and wherein each performance category corresponds to at least one controllable audio feature of the first set of controllable audio features.

15. The system of claim 1, wherein the one or more processors are further configured to determine the deviation type by using an artificial intelligence to compare the plurality of measurements and the corresponding plurality of user-specific target measurements.

16. The system of claim 1, wherein the one or more processors are further configured to determine the deviation value based on weighted differences between the plurality of measurements and the corresponding plurality of user-specific target measurements.

17. The system of claim 1, wherein the at least one sensor is a first sensor, and wherein the system further comprises a second sensor on a sound limb of the wearer, wherein the sensor motion data is from the first sensor and the second sensor.

18. A computer-implemented method to modify an audio signal that is to be provided to a subject in response to changes in motion patterns of the subject, the method comprising:
identifying a first performance activity for assessment;
consulting a memory to identify a first set of motion characteristics and a first set of controllable audio features associated with the first performance activity, wherein the memory associates a plurality of performance activities with a plurality of motion characteristics and a plurality of controllable audio features, wherein a particular performance activity of the plurality of performance activities is associated with a particular set of motion characteristics of the plurality of motion characteristics and a particular set of controllable audio features of the plurality of controllable audio features, wherein the first set of motion characteristics comprises multiple motion characteristics of the plurality of motion characteristics;
receiving the audio signal from a source;
receiving sensor motion data from at least one sensor coupled to a leg prosthesis worn by the subject;
determining a plurality of measurements for the first set of motion characteristics based on the sensor motion data;
determine a deviation value and a deviation type by comparing the plurality of measurements to corresponding baseline measurements and target measurements wherein the baseline measurements and the target measurements are different and are generated based at least in part on measurements associated with a prior performance of the first performance activity by the subject;
based at least in part on a determination that the deviation value is greater than a first deviation threshold and less than a second deviation threshold, modifying the audio signal by adjusting at least one controllable audio feature of the first set of controllable audio features of the audio signal by a first amount, wherein the first deviation threshold is based at least in part on the target measurements, and the second deviation threshold is greater than the first deviation threshold and is based at least in part on the baseline measurements, and wherein the at least one controllable audio feature is based at least in part on the deviation type; and
based at least in part on a determination that the deviation value is greater than the second deviation threshold, modify the received audio signal by adjusting the at least one controllable audio feature of the first set of controllable audio features by a second amount, wherein the second amount is greater than the first amount.

19. The method of claim 18, wherein the at least one controllable audio feature of the first set of controllable audio features corresponds to at least one of amplitude modulation, frequency modulation, distortion, bitcrushing, chorus, ducking, frequency filtering, spatialization, localization, panning, reverb, echo, compression, phasing, flanging, gating, vocoding, or delay on the audio signal.

20. The method of claim 19, wherein the frequency filtering corresponds to at least one of a high-pass filtering, bass-cut filtering, a band-pass filtering, a low-shelf filtering, a high-shelf filtering, or a band-stop filtering.

21. The method of claim 18, wherein the audio signal includes music, wherein the modified audio signal approaches the received audio signal as the deviation value approaches zero.

22. The method of claim 18, wherein the first set of motion characteristics comprises at least one of gait speed, step width, step length, stance time, gait phase, symmetry of limbs, inertial motions of the limbs, cadence, path of pressure, path of center of mass, ground reaction force, lower limb or sacral trajectory, or trunk orientation.

23. The method of claim 18, wherein the first set of motion characteristics comprises at least one trunk flexion, trunk extension, hip flexion, hip extension, knee flexion, knee extension, foot-floor angle at heel contact, ankle plantarflexion, ankle dorsiflexion, or energy expenditure.

24. The method of claim 18, wherein the at least one controllable audio feature of the first set of controllable audio features comprises at least two controllable audio features.

25. The method of claim 18, wherein the first set of motion characteristics comprises at least two different motion characteristics.

26. The method of claim 18, wherein the plurality of measurements is automatically classified into a performance category, wherein the performance category corresponds to at least one of sub-par performance or acceptable performance, and wherein each performance category corresponds to at least one controllable audio feature of the first set of controllable audio features.

27. The method of claim 18, wherein the deviation type is determined by using an artificial intelligence to compare the plurality of measurements and the corresponding baseline measurements and the target measurements.

28. The method of claim 18, wherein the at least one sensor is a first sensor, and wherein the sensor motion data is received from the first sensor and a second sensor on a sound limb of the subject.

29. A non-transitory computer-readable storage medium storing computer-executable instructions that when executed by one or more processors cause the one or more processors to:
identify a first performance activity for assessment;
consult a memory to identify a first set of motion characteristics and a first set of controllable audio features associated with the first performance activity, wherein the memory associates a plurality of performance activities with a plurality of motion characteristics and a plurality of controllable audio features, wherein a particular performance activity of the plurality of performance activities is associated with a particular set of motion characteristics of the plurality of motion characteristics and a particular set of controllable audio features of the plurality of controllable audio features, wherein the first set of motion characteristics comprises multiple motion characteristics of the plurality of motion characteristics;
receive an audio signal from a source;
receive sensor motion data that corresponds to a subject;
determine a plurality of measurements for the first set of motion characteristics based on the sensor motion data;

determine a deviation value and deviation type based on differences between the plurality of measurements and corresponding subject-specific target measurements and subject-specific baseline measurements, wherein the corresponding subject-specific target measurements are generated based at least in part on measurements associated with a prior performance of the performance activity by the subject;

based at least in part on a determination that the deviation value is greater than a first deviation threshold that corresponds to the subject-specific target measurements and less than a second deviation threshold that is greater than the first deviation threshold and that corresponds to the subject-specific baseline measurements, modify the audio signal by adjusting at least one controllable audio feature of the first set of controllable audio features of the audio signal by a first amount, wherein the at least one controllable audio feature is based at least in part on the deviation type; and based at least in part on a determination that the deviation value is greater than the second deviation threshold, modify the received audio signal by adjusting the at least one controllable audio feature of the first set of controllable audio features by a second amount that is greater than the first amount.

30. The non-transitory computer-readable storage medium of claim 29, wherein the sensor motion data corresponds to data received from a sensor coupled to a leg prosthesis worn by the subject.

31. The non-transitory computer-readable storage medium of claim 29, wherein the plurality of measurements is automatically classified into a performance category, and wherein each performance category corresponds to at least one controllable audio feature of the first set of controllable audio features.

32. The non-transitory computer-readable storage medium of claim 29, the deviation value is determined based on weighted differences between the plurality of measurements and the corresponding subject-specific target measurements and the subject-specific baseline measurements.

* * * * *